United States Patent [19]

Gautier et al.

[11] Patent Number: 5,031,603

[45] Date of Patent: Jul. 16, 1991

[54] URETERO-RENOSCOPE

[75] Inventors: Jean-Romain Gautier, Toulouse, France; Ludwig Bonnet, Knittlingen, Fed. Rep. of Germany

[73] Assignee: Richard Wolf GmbH, Knittlingen, Fed. Rep. of Germany

[21] Appl. No.: 493,034

[22] Filed: Mar. 12, 1990

[30] Foreign Application Priority Data

Apr. 19, 1989 [DE] Fed. Rep. of Germany ....... 3912797

[51] Int. Cl.⁵ .............................................. A61B 1/00
[52] U.S. Cl. ........................................... 128/4; 128/7
[58] Field of Search ................................ 128/4, 5, 6, 7

[56] References Cited

U.S. PATENT DOCUMENTS

| | | | |
|---|---|---|---|
| 4,606,330 | 8/1986 | Bonnet | 128/7 |
| 4,685,449 | 8/1987 | Bonnet | 128/4 |
| 4,807,595 | 2/1989 | Hiltebrandt | 128/4 |
| 4,986,258 | 1/1991 | Cho et al. | 128/7 |

*Primary Examiner*—William H. Grieb
*Attorney, Agent, or Firm*—Panitch Schwarze Jacobs & Nadel

[57] ABSTRACT

A uretero-renoscope assembly comprises a first shaft to accommodate an optical system and an auxiliary instrument passage, this first shaft being connected at its proximal end to a housing provided with connections for a light conductor cable and for the infeed or discharge of flushing fluid or the like. The first shaft has a cross-sectional area which decreases in steps in the distal direction, and has a circular cross-section at its proximal end which merges into an oval cross-section at the distal end. A second shaft of circular cross-section can be pushed onto the first, with the first shaft in position in the ureter after withdrawal of the uretero-renoscope, forming a further stepped increase in cross-section and providing a further passage, for example for flushing fluid.

6 Claims, 1 Drawing Sheet

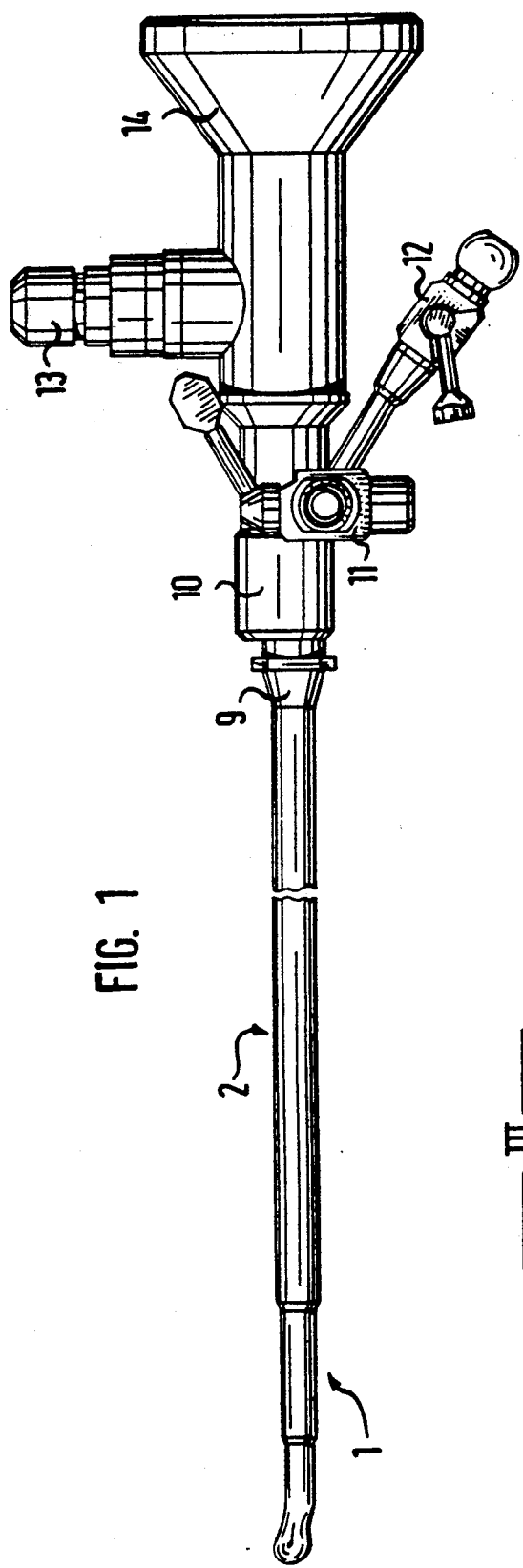
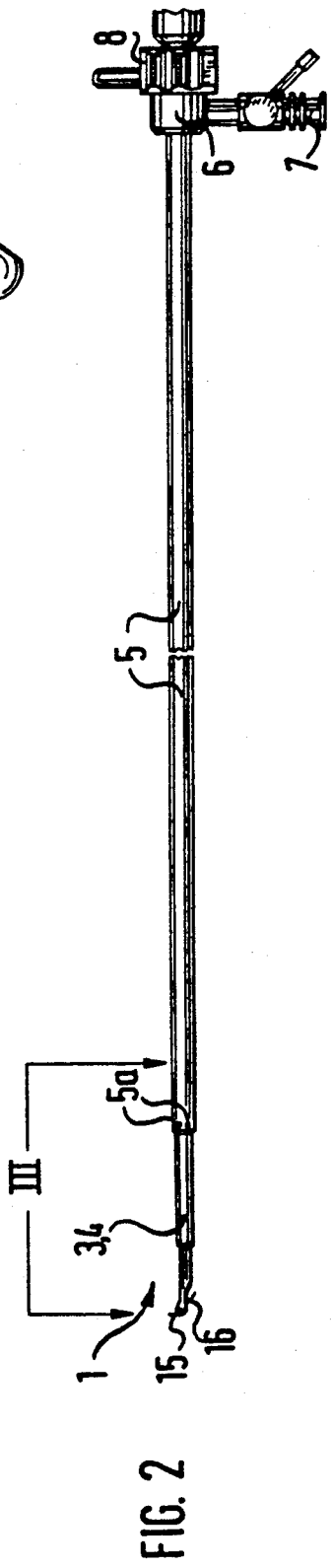
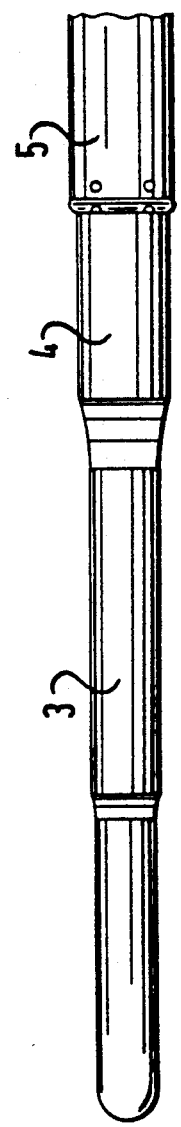

URETERO-RENOSCOPE

BACKGROUND OF THE INVENTION

The invention relates to a uretero-renoscope of the type comprising a shaft with an instrument passage therethrough intended to be traversed by auxiliary instruments and a housing connected to the shaft for connection of a light conducting cable as well as connectors for the infeed and discharge of a flushing fluid or the like.

DESCRIPTION OF THE PRIOR ART

German utility model No. 83 22 900 (U.S. Pat. No. 4,606,330) discloses an instrument of this type of which the shaft is narrowed with respect to its proximal section, to obtain as low a stress as possible on the ureter by reducing the diameter in the distal portion of the shaft on the one hand and, on the other hand, to secure an adequate mechanical strength by enlarging the diameter of the shaft at its proximal end.

German patent No. 35 04 252 U.S. Pat. No. 4,685,449 also discloses a uretero-renoscope comprising a shaft which is stepped once and forms with optical system, a unit which can be disconnected from a distal portion of the shaft to allow a second optical system to be inserted into the said distal portion while the latter remains in the ureter, for example an optical system having a direction of sight differing from the first. The necking down of the shaft is to this end adapted to the diameter of the ureter, while maintaining adequate strength.

These prior art uretero-renoscopes have the disadvantage that on the one hand the insertion of the shaft into the ureter through the ureter ostium cannot be performed without preliminary dilation of the ostium and without an obturator inserted into the instrument passage despite the reduction in the shaft diameter over part of its length, and on the other hand the dilating action quite substantially lengthens the period of endoscopic intervention, so that there may well be traumatisation of the ostium caused by the dilation. Another disadvantage of the prior art devices is that the oval instrument cross-section optimised in view of the available unoccupied ureter volume is usable only for the passage of instruments having a comparatively small circular cross-section, so that a substantial part of the available space cannot be exploited under particular conditions or it is impossible to use instruments having a larger external diameter, because of special application methods, in combination with the prior art shafts.

SUMMARY OF THE INVENTION

It is accordingly an object of the invention to provide a uretero-renoscope assembly which is so formed that it may be inserted into and through the ostium without making use of an additional dilator and obturator and that this insertion as well as the continued insertion of the uretero-renoscope as far as the pelvis of the kidney and if appropriate the upper calyx groups, may be performed under constant visual inspection. It is a further object of the invention to provide means for replacing the uretero-renoscope by a different instrument if need be, which fully utilises the available space of the complementary shaft remaining within the ureter.

According to the invention, this object is achieved in that a first shaft of the uretero-renoscope assembly is formed with a plurality of successive steps enlarging its cross-section as seen in the proximal direction and endowed with an oval cross-section in the region of its distal end, which is dimensioned as a function of the minimum technically attainable diameter of the optical system and an additional instrument passage of minimal diameter and that the cross-section - starting from this shaft portion — merges into a circular cross-section in the proximal direction and in that an additional tubular shaft is releasably secured to the final step section, which also has a circular cross-section.

It is a particular advantage of the present invention that by virtue of the small cross-section of the distal end of the uretero-renoscope shaft, the shaft may be inserted without difficulty into and through the ostium and into the ureter without causing creases to be formed by the upward displacement of the ureter. The multiple gradation of the distal end of the shaft moreover ensures that a gentle and gradual dilation occurs, which in particular does not cause trauma of the ostium and can be effected under simultaneous visual inspection through the optical system.

Because the uretero-renoscope of the invention also acts as a dilator, it is advantageously unnecessary to dilate the ostium, which tends to revert to size, beyond the degree required or to leave a catheter or the like in place to maintain the aperture cross-section.

Thanks to the invention, it is thereby possible for the first time to perform a gentle dilation, without causing trauma to the ostium, and thereupon immediately to undertake a visual inspection of the ureter and/or an endoscopic intervention which may be needed under particular circumstances. Also of importance is the fact that the patient is exposed to less injury, to a degree which should not be underestimated, as well as to a reduced risk of infection, thanks to the shorter period of therapy.

The additional tubular shaft is preferably pushed over the proximal end portion of the stepped shaft and provides an increase in the mechanical strength of the renoscope shaft. The additional shaft can also simultaneously act as a dilator. In addition, flushing fluid may be supplied and drawn off through it and it can be used to perform other treatments as required thanks to its releasable fastening on the renoscope shaft. For example the uretero-renoscope may be withdrawn from the shaft to allow the insertion into the ureter of a ureterotome for cutting a ureter stenosis.

Further objects and advantageous features of the invention will become apparent from the following detailed description when read in conjunction with the accompanying drawings which illustrate a preferred embodiment.

BRIEF DESCRIPTION OF THE DRAWINGS

In the drawings:

FIG. 1 is a side view of a uretero-renoscope according to a preferred embodiment of the invention, without the additional shaft which may be slid on to it;

FIG. 2 shows on a reduced scale the shaft according to FIG. 1, with its additional shaft in place; and FIG. 3 is an enlarged plan view in the direction of the arrow 3 in FIG. 2.

DETAILED DESCRIPTION OF THE PREFERRED EMBODIMENT

The uretero-renoscope assembly 1, FIGS. 1 and 2, essentially comprises a comparatively thin elongated shaft 2 with proximal and distal portions, its distal portion (shown on the left in FIG. 1) having several shaft steps 3 and 4 following one another. To this end, the distal shaft portion has an atraumatically formed leading end and has an oval cross-section followed in the proximal direction by a shaft portion 3 of similarly oval cross-section, which in turn merges into a shaft section 4 of circular cross-section. This shaft section 4 has pushed coaxially on to it, as shown in FIG. 2, a tubular shaft 5 which has a rotary coupling element 6 comprising a cutoff tap 7 at its proximal end and several openings 5a in its distal end, for the infeed and/or withdrawal of a flushing fluid or the like. The rotary coupling element 6 is releasably securable in a coupling element 9 by means of a clamping ring 8, which coupling element can be secured to a housing 10 mounted on the proximal end of the shaft section 4. The housing 10 is provided with one or more coupling connectors 11, an insertion connector 12 and a coupling 13 to receive a light conducting cable connection element and also serves to receive an eyepiece with an ocular cone 14 of an image transmission system which is not illustrated in detail.

As is apparent from FIG. 2, there is situated at the leading end of the shaft 2 an objective opening 15 for the optical system integrated in the shaft 2, as well as the outlet end of a passage 16 through the shaft, intended for the insertion of the instruments and other operating devices.

Thanks to the steps 3 and 4, the uretero-renoscope may be inserted through the ostium and into the ureter without the need for an initial dilation and without an additional obturator. In addition, the auxiliary shaft 5, of circular cross-section, can be slid over, and releasably secured on, the proximal portion of shaft 2, also of circular cross-section, while the shaft remains in situ in the ureter after withdrawal of the uretero-renoscope. This increases the strength of the assembly and allows other instruments to be inserted as desired. The rounded shape of the leading end of the shaft 5 enables it to pass through the ostium into the ureter without any separate dilation step, thus reducing the risk of trauma to the ostium.

What is claimed is:

1. A uretero-renoscope comprising:
   a first shaft for an optical system, said shaft having proximal and distal ends and having a cross-section which reduces in a plurality of steps from said proximal end to said distal end, said first shaft having a distal end portion of oval cross-section which merges in a direction towards said proximal end into a portion of circular cross-section;
   an additional instrument passage formed through said first shaft;
   a housing connected to said first shaft at its proximal end and having thereon connection means for a light conductor cable and inlet and outlet means for a flushing fluid;
   a second shaft of larger cross-section than the first shaft and releasably securable to said first shaft, at a proximal position relative to said steps, to form an additional step and
   coupling means on said housing for releasably securing said second shaft thereto.

2. A uretero-renoscope as claimed in claim 1 wherein said second shaft is of circular cross-section and is shaped and dimensioned to be pushed onto said first shaft.

3. A uretero-renoscope as claimed in claim 1 wherein said coupling means for the second shaft comprises a coupling cone on a distal end portion of said housing.

4. A uretero-renoscope as claimed in claim 3 wherein said second shaft is provided with a clamping ring which is releasably attachable to said coupling cone to secure the second shaft releasably to the housing at a proximal end portion of the shaft.

5. A uretero-renoscope as claimed in claim 1 wherein said second shaft has a proximal end provided with coupling means and a distal end provided with openings for the passage of fluid.

6. A uretero-renoscope as claimed in claim 1 wherein said steps are spaced from one another at intervals of about 5 to 50 mm.

* * * * *